United States Patent

Moser

Patent Number: 5,211,062
Date of Patent: May 18, 1993

[54] CHIP SAMPLING DEVICE

[75] Inventor: Robert H. Moser, Omaha, Nebr.

[73] Assignee: InterSystems, Inc., Omaha, Nebr.

[21] Appl. No.: 769,468

[22] Filed: Oct. 1, 1991

[51] Int. Cl.$^5$ .............................................. G01N 1/00
[52] U.S. Cl. ............................. 73/864.33; 73/864.34;
73/863.83
[58] Field of Search ........... 73/863.32, 863.83, 864.33,
73/864.34, 864.35, 864.41–864.45, 864.73,
864.74

[56] References Cited

U.S. PATENT DOCUMENTS

| 2,167,393 | 7/1939 | Muncy | 255/24 |
| 2,492,158 | 12/1947 | Compte et al. | 73/864.44 |
| 3,262,318 | 7/1966 | Decker | 73/421 |
| 3,580,084 | 5/1971 | Kramer | 73/421 |
| 4,088,025 | 5/1978 | Foster et al. | 73/423 |
| 4,616,515 | 10/1986 | Dancoine | 73/863.82 |
| 4,743,155 | 5/1988 | Carey et al. | 73/863.51 |
| 4,936,153 | 6/1990 | Klit | 73/864.33 |

Primary Examiner—Robert Raevis
Attorney, Agent, or Firm—Zarley, McKee, Thomte, Voorhees & Sease

[57] ABSTRACT

A chip sampling device comprising a sampling probe including an outer rotatable tube having an inner tube positioned therein. The upper end of the inner tube is in communication with a source of vacuum so that chips will be drawn into the lower end of the inner tube. The lower end of the inner tube is provided with serrations provided at the lower end thereof while the lower end of the outer tube is provided with serrations and inwardly extending fingers. The rotation of the outer tube and the action of the various serrations and fingers prevents the chips from plugging the lower end of the outer tube or from plugging the lower end of the inner tube.

8 Claims, 4 Drawing Sheets

CHIP SAMPLING DEVICE

BACKGROUND OF THE INVENTION

This invention relates to a sampling device and more particularly to a wood chip sampling device.

Many types of sampling devices have been previously provided for collecting samples from a load of grain, etc. The original sampling devices consisted of a probe which was manually inserted into the load with the compartments in the probe then being opened to permit the sampling of the commodity. Realizing that the manual operation was less than satisfactory, pneumatic sampling devices were then provided. For example, see U.S. Pat. No. 4,936,153. Although the devices of the prior art may work satisfactorily in collecting samples from grain, the conventional devices do not operate efficiently or satisfactorily when it is desired to gather samples from a load of wood chips. The wood chips are difficult to sample in that they tend to plug or clog the lower end of the sampling probe. Further, the devices of the prior art do not permit the sampling of the wood chips located near the bottom of the vessel.

It is therefore a principal object of the invention to provide an improved chip sampling device.

Still another object of the invention is to provide a chip sampling device including an outer rotatable tubular member having an inner tubular member positioned therein with the lower ends of both tubes having irregular surfaces thereon to prevent plugging of the sampling probe.

Yet another object of the invention is to provide a chip sampling device which permits the sampling of the chips throughout the load.

Yet another object of the invention is to provide a chip sampling device which is easy to use, durable and economical of manufacture.

These and other objects of the present invention will be apparent to those skilled in the art.

SUMMARY OF THE INVENTION

A Chip sampling system is described comprising a sampling probe which may be moved downwardly into a load of wood chips so as to be able to withdraw a sample of the chips from desired locations throughout the load. The probe permits sampling all the way through the load to the bottom of the vessel. The sampling probe comprises an outer rotatable tubular member having an open lower end. An inner tubular member is positioned within the outer tubular member and has its lower end disposed above the lower end of the outer tubular member. The inner tubular member is in communication with a source of vacuum pressure so that wood chips will be drawn into the lower end of the outer tubular member and upwardly through the inner tubular member. The lower end of the outer tubular member is provided with a chip agitation means provided thereon as is the lower end of the inner tubular member. The chip agitation means on the inner and outer tubular members cooperate to prevent the chips from plugging the lower end of the outer tubular member or the lower end of the inner tubular member.

DESCRIPTION OF THE PREFERRED EMBODIMENT

Figure 1:
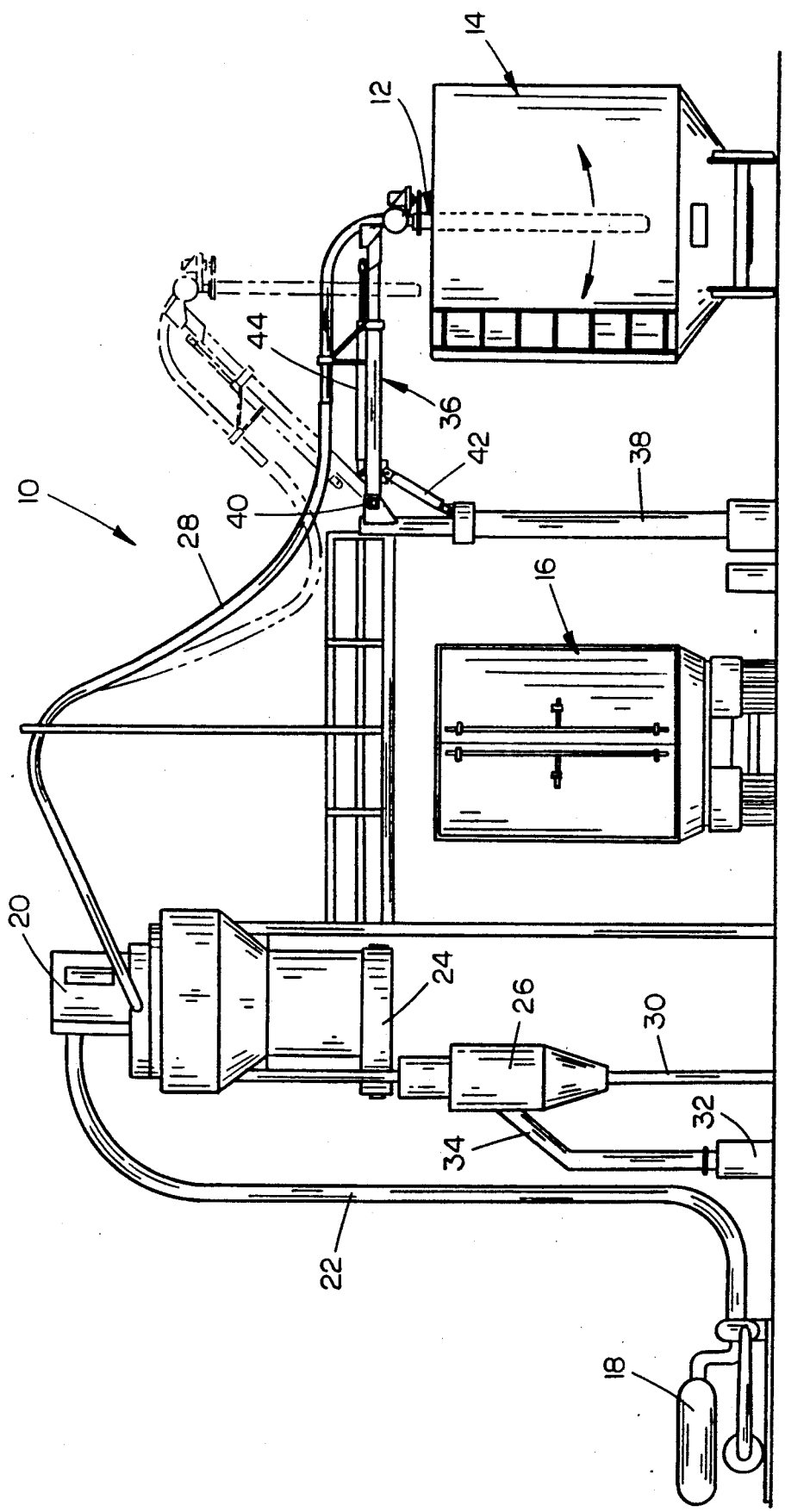
FIG. 1 is a view illustrating the chip sampler of this invention lowered into a load of chips.
Figure 2:
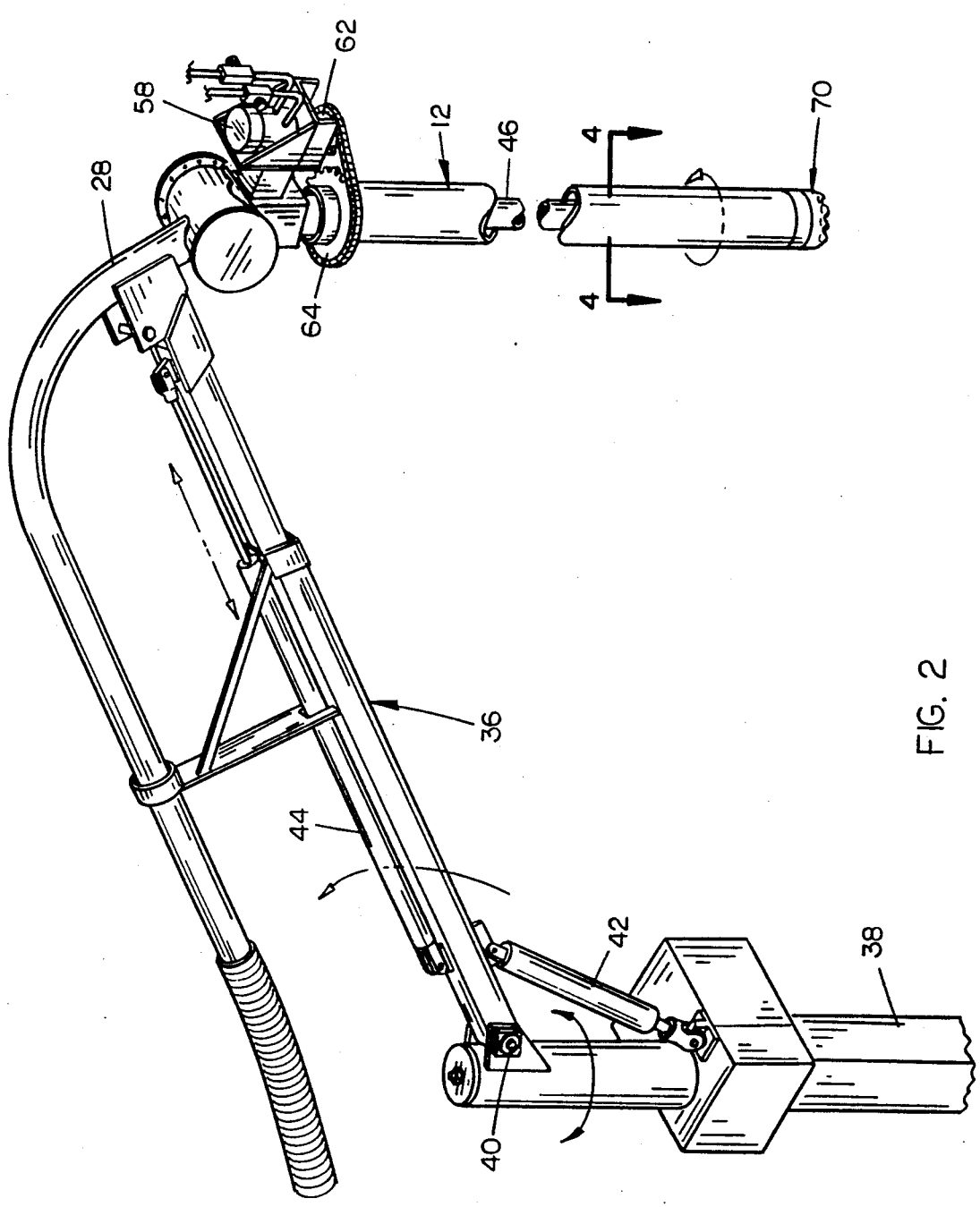
FIG. 2 is a perspective view of the chip sampler of this invention.

The numeral 10 refers generally to the chip sampling system of this invention which includes many conventional components. It is the sampling probe 12 which comprises the invention with the remaining components permitting the probe 12 to function. With respect to FIG. 1, the numeral 14 refers to a rail car or the like which contains a load of wood chips to be sampled. The numeral 16 refers to a truck containing a load of wood chips to be sampled.

The numeral 18 refers generally to a conventional pneumatic power train with motor, positive displacement blower, air silencer, belt drive and vacuum relief vent. Power train 18 is connected to a conventional collector 20 by pneumatic tube 22. Collector 20 comprised of a pneumatic conveying intercept hopper with final dust collector and automatic bag shaker. Located below collector 20 is a conveyor/feeder 24 which is in operative communication with a sample divider 26. Probe 12 is operatively connected to collector 20 by means of the pneumatic tube or hose 28 so that the collected sample is directed to the collector. After passing through the collector 20, the wood chips are conveyed or fed by the conveyor/feeder 24 to the upper end of the sample divider 26. The divider 26 splits the sample to an amount necessary for an analysis and the balance of the sample is returned to the transport by means of the pneumatic hose or line 30. The collected sample is conveyed from the divider 26 to the sample container 32 by conduit 34.

Probe 12 is mounted on the outer end of a telescoping and pivotal boom 36 which is pivotally connected to the support 38 at 40. Hydraulic cylinder 42 is provided for raising and lower the probe 12 as illustrated by the broken lines in FIG. 1. Hydraulic cylinder 44 is provided for laterally moving the probe 12 with respect to the support 38.

Probe 12 includes an inner tube 46 which has its end in communication with manifold 48 which is in vacuum communication with the vacuum line 28. The lower end of tube 46 terminates in a wall member 50 which extends inwardly and downwardly and which is provided with a plurality of serrations or notches 52 in its lower end.

Probe 12 also includes an outer tube 54 which is rotatably mounted on the flange 56 of tube 46 and which is rotated relative to tube 46 by means of motor 58. Motor 58 includes a power shaft 60 having sprocket 62 mounted thereon. Sprocket 64 is mounted on the exterior surface of tube 54 and has a chain 66 extending therearound which also extends around sprocket 62 so that actuation of motor 58 causes tube 54 to be rotated with respect to tube 46.

Figure 3:
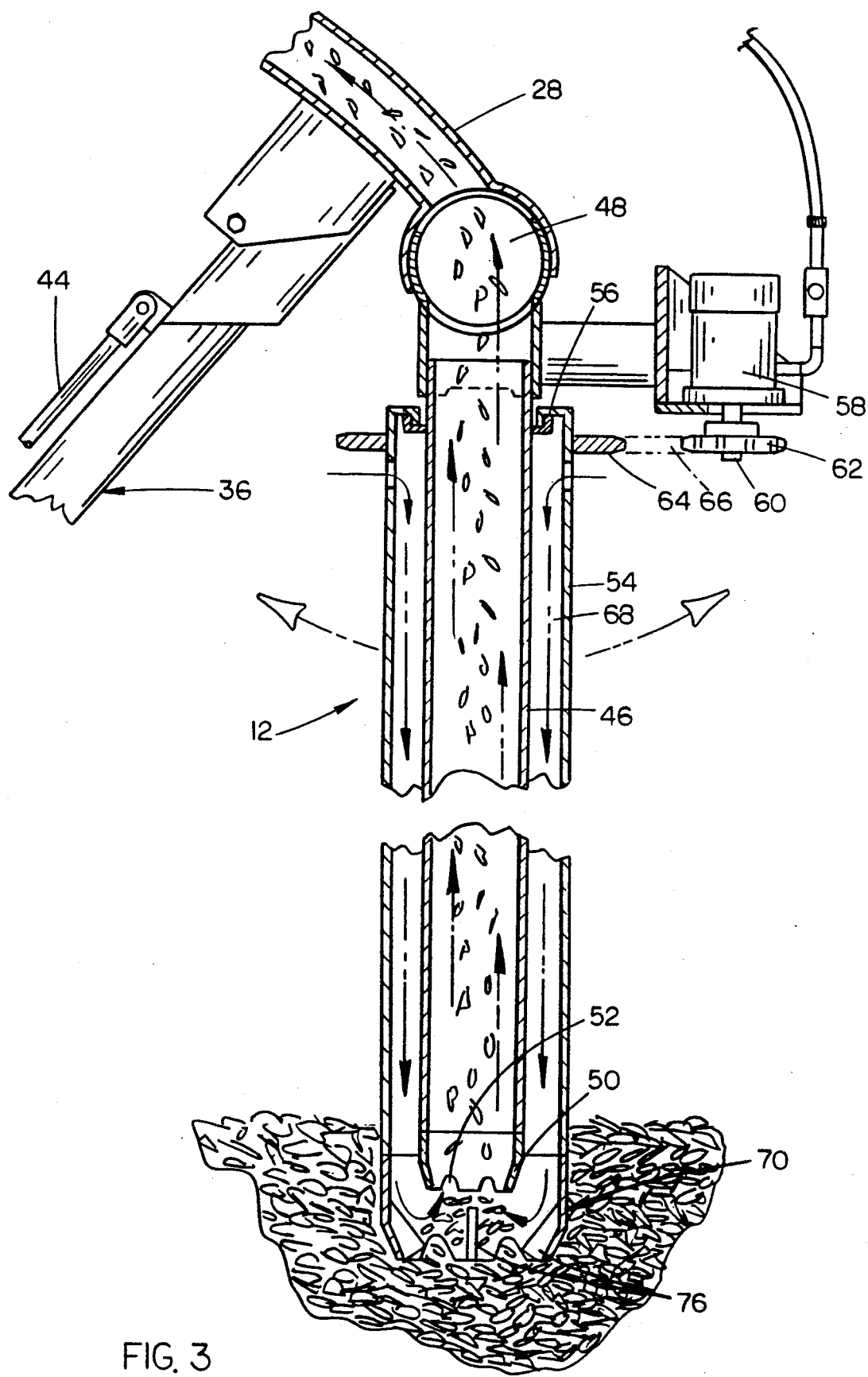
FIG. 3 is a vertical sectional view of the chip sampling probe of this invention.
Figure 4:
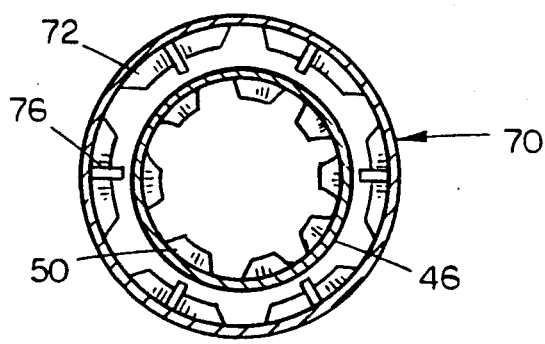
FIG. 4 is a sectional view as seen on lines 4—4 of FIG. 2.
Figure 5:
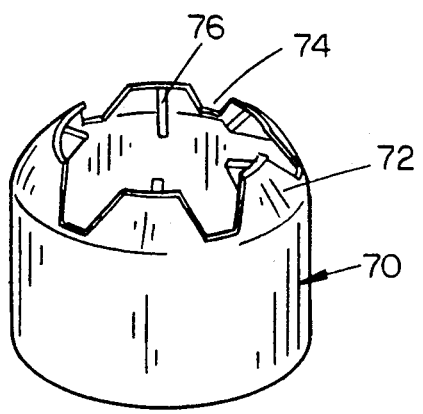
FIG. 5 is a perspective view of the lower end of one form of the outer tube.

The upper end of tube 54 is in communication with the atmosphere so that the air may be drawn downwardly into the annular space between tubes 46 and 54 which is referred generally by the reference numeral 68. The lower end of tube 54 is provided with a chip agitating means referred to generally by the reference number 70 which may take many forms although certain of the forms or embodiments are preferred. FIG. 5 illustrates the preferred embodiment of the chip agitation means 70 and it can be seen that the lower end of chip agitation means 70 terminates in a wall member 72 which extends inwardly and downwardly and which has a plurality of serrations 74 provided in the lower end thereof. A plurality of fingers 76 extend inwardly from the inside surface of the lower end of chip agitation means 70 as illustrated in FIGS. 3 and 5.

Figure 6:
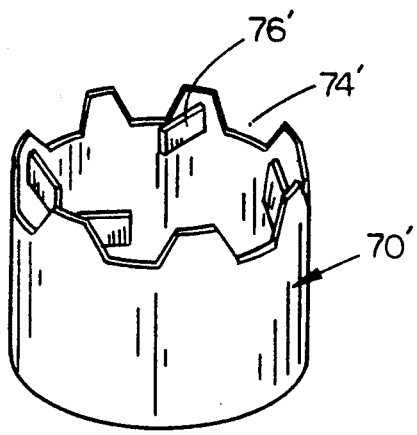
FIG. 6 is a view similar to FIG. 5 but which illustrates a modified form of the invention.

A modified form of the chip agitation means is illustrated in FIG. 6 and is referred to generally by the reference numeral 70'. The lower end of agitation means 70' does not taper inwardly but is a straight wall portion having a plurality of serrations 74' provided therein. A plurality of fingers 76' extend inwardly from the interior surface of the agitation means 70' as illustrated in FIG. 6.

Figure 7:
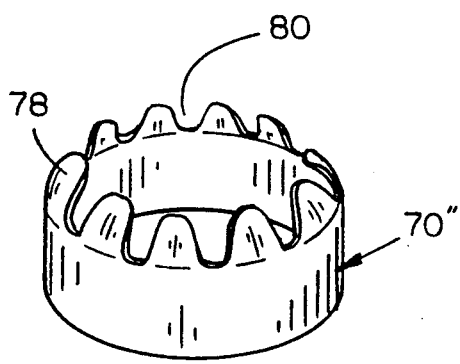
FIG. 7 is a view similar to FIGS. 5 and 6 but which illustrates yet another embodiment of the invention.
Figure 8:
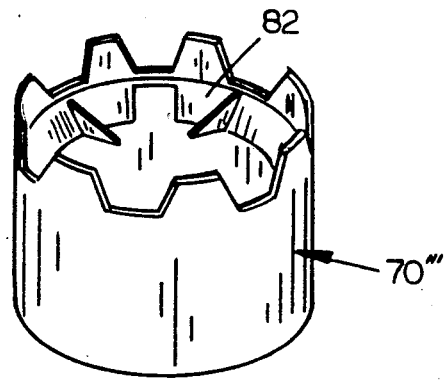
FIG. 8 is a view similar to FIGS. 5, 6 and 7 but which illustrates yet another embodiment of the invention.

Yet another form of the chip agitation means illustrated in FIG. 7. It can be seen that the chip agitation means 70" in FIG. 7 does not have inwardly extending fingers as do the embodiments of FIGS. 5 and 6. Although the chip agitation means of FIG. 7 will work in some situations, it is preferred that fingers such as fingers 76 or 76' be utilized. As seen in FIG. 7, agitation means 70" includes an inwardly and downwardly extending wall member 78 having a plurality of serrations or openings 80 formed therein. FIG. 8 illustrates yet another embodiment of the agitation means which is referred to generally by the reference number 70'''. Agitation means 70''' is similar to agitation means 70' except that the fingers 83 extend inwardly from short wall members 82.

In operation, the probe 12 is lowered into the load of wood chips while the outer tube 54 is rotated by the motor 58 while vacuum is being applied to the upper end of the inner end of tube 46. If it is desired to begin the sampling process after the lower end of the probe has reached a particular depth in the load, vacuum would not be applied to the upper end of tube 46 until the lower end of the probe has reached the predetermined position. The design of the probe permits sampling throughout the entire load and permits sampling at the bottom of the vessel.

The rotation of the tube 54 causes the serrations, irregular surfaces and fingers at the lower end thereof to penetrate through the wood chips. The chip agitation means 70 cooperates with the serrated lower end of the tube 46 to prevent the chips from plugging or clogging the lower end of tube 54 or the lower end of tube 46. Without the chip agitation means, it would be impossible to efficiently obtain a sample of the chips due to the size and consistency of the chips.

Thus it can be seen that the invention accomplishes at least all of its stated objectives.

I claim:

1. A chip sampling system for taking samples from a load of wood chips, the sampling system comprising,
    a substantially vertically disposed sampling tube means adapted to be lowered downwardly into the load of wood chips,
    said sampling tube means comprising an outer tube having an inner tube positioned therein, said inner and outer tubes defining an annular space therebetween,
    vacuum means in communication with the upper end of said inner tube for drawings chips into the interior of said inner tube,
    means for rotating said outer tube with respect to said inner tube,
    and a chip agitator means on the lower end of said outer tube for agitating the chips being drawn into said inner tube.

2. The chip sampling system of claim 1 wherein the lower end of said inner tube has an irregular surface.

3. The chip sampling system of claim 1 wherein the lower end of said inner tube is scalloped.

4. The chip sampling system of claim 1 wherein said chip agitator means comprises an annular wall which extends downwardly and inwardly from the lower end of said outer tube.

5. The chip sampling system of claim 4 wherein the lower end of said annular wall is scalloped.

6. The chip sampling system of claim 4 wherein the lower end of said annular wall has an irregular surface.

7. The chip sampling system of claim 4 wherein said annular wall has inner and outer surfaces and wherein a plurality of spaced-apart fingers are mounted on the inner surface of said annular wall.

8. The chip sampling system of claim 4 wherein the lower end of said annular wall has a plurality of notches formed therein.

* * * * *